(12) United States Patent
Dedick et al.

(10) Patent No.: US 12,018,391 B1
(45) Date of Patent: Jun. 25, 2024

(54) GENERATION OF STRUCTURALLY ALTERED GAS MOLECULES FROM WATER AND APPLICATION THEREOF

(71) Applicants: H2Plus LLC, San Diego, CA (US); H2Plus Operations, LLC, San Diego, CA (US)

(72) Inventors: Gene Dedick, Grand Junction, CO (US); Gustav Eriksson, St. Pete Beach, FL (US); Jared Roberts, Grand Junction, CO (US); David Hauschild, Phoenix, AZ (US)

(73) Assignees: H2Plus LLC Operations, LLC, San Diego, CA (US); H2Plus Operations, LLC, San Diego, CA (US)

( * ) Notice: Subject to any disclaimer, the term of this patent is extended or adjusted under 35 U.S.C. 154(b) by 0 days.

(21) Appl. No.: 18/518,525

(22) Filed: Nov. 23, 2023

Related U.S. Application Data

(60) Division of application No. 18/376,790, filed on Oct. 4, 2023, now Pat. No. 12,000,053, which is a continuation-in-part of application No. PCT/US2022/044167, filed on Sep. 21, 2022, which is a continuation of application No. 17/487,613, filed on Sep. 28, 2021, now Pat. No. 11,384,440, said application No. 18/376,790 is a continuation-in-part of application No. PCT/US2022/044168, filed on Sep. 21, 2022, which is a continuation of application
(Continued)

(51) Int. Cl.
| | |
|---|---|
| B01J 19/08 | (2006.01) |
| B01J 19/12 | (2006.01) |
| C01B 5/00 | (2006.01) |
| C25B 1/04 | (2021.01) |
| C25B 15/027 | (2021.01) |

(52) U.S. Cl.
CPC .............. *C25B 1/04* (2013.01); *B01J 19/12* (2013.01); *C01B 5/00* (2013.01); *C25B 15/027* (2021.01)

(58) Field of Classification Search
CPC .......... C25B 1/04; C25B 15/027; B01J 19/12; C01B 5/00
See application file for complete search history.

(56) References Cited

U.S. PATENT DOCUMENTS

| | | | |
|---|---|---|---|
| 10,626,036 B1 * | 4/2020 | Guoin | B01F 25/43161 |
| 11,384,440 B1 * | 7/2022 | Roberts | C25B 1/04 |

(Continued)

*Primary Examiner* — Zulmariam Mendez
(74) *Attorney, Agent, or Firm* — Georgiy L. Khayet

(57) ABSTRACT

Methods and systems for generation and deployment of a structurally altered gas molecules derived from water are provided. An example system includes a first container for combining purified water with a compound mixture being non-reactive with the water and a conductor of an electric field and a magnetic field. The system includes a magnetic field generator and an electric field generator designed to apply the magnetic field and the electric field to the combination of the purified water and the compound mixture to cause generation of the structurally altered gas molecules having a higher probability of attraction of electrons into areas adjunct to the structurally altered gas molecules than molecules of the purified water. The system further includes a second container for introducing the structurally altered gas molecules into an environment of a chemical process to facilitate electron transfers during the chemical process, thereby increasing output of the chemical process.

12 Claims, 13 Drawing Sheets

Related U.S. Application Data

No. 17/743,632, filed on May 13, 2022, now Pat. No. 11,634,823, which is a continuation of application No. 17/487,613, filed on Sep. 28, 2021, now Pat. No. 11,384,440, said application No. PCT/US2022/044168 is a continuation of application No. 17/487,613, filed on Sep. 28, 2021, now Pat. No. 11,384,440.

(56) References Cited

U.S. PATENT DOCUMENTS

| | | | |
|---|---|---|---|
| 2016/0326660 A1* | 11/2016 | Chiou | C25B 15/02 |
| 2017/0368528 A1* | 12/2017 | Gourley | C25B 9/05 |

* cited by examiner

| Components | Mol % | Wt. % | at 14.696 psia |
|---|---|---|---|
| Hydrogen | 67 | 11.3 | |
| Oxygen | 33 | 88.7 | |
| Helium | NIL | NIL | |
| Carbon Monoxide | NIL | NIL | |
| Carbon Dioxide | NIL | NIL | |
| Sulfur | NIL | NIL | |
| Nitrogen | NIL | NIL | |
| Methane | NIL | NIL | |
| Ethane | NIL | NIL | |
| Ethylene | NIL | NIL | |
| Propane | NIL | NIL | |
| Propylene | NIL | NIL | |
| ISO-Butane | NIL | NIL | |
| n-Butane | NIL | NIL | |
| Propadiene | NIL | NIL | |
| Trans-2-Butene | NIL | NIL | |
| 1-Butene | NIL | NIL | |
| ISO-Butylene | NIL | NIL | |
| CIS-2-Butene | NIL | NIL | |
| NEO Pentane | NIL | NIL | |
| ISO-Pentane | NIL | NIL | |
| n-Pentane | NIL | NIL | |
| 1,3 Butadiene | NIL | NIL | |
| Hexanes Plus | NIL | NIL | |

FIG. 4

Comparable Gas Specifications

| | NATURAL GAS | HYDROGEN | GAS |
|---|---|---|---|
| HHV MJ/kg | 52.20 | 141.70 | 172.87 |
| Energy Density (MJ*Kg/SM3) | 37.43 | 12.75 | 89.03 |
| Atomic Mass (g/mol) | 16.04 | 1.01 | 12.16 |
| Density (Kg/SM3) | 0.72 | 0.09 | 0.52 |
| HHV (MJ/M3 at 200 bar) | 39.76 | 12.76 | 97.93 |
| Volume (AMU/Density at SM3) (SM3 at 1.01325 bar, 15C) | 22.37 | 11.20 | 23.61 |
| Liquid to Gas volume ratio (14.696 psig) | 600 | 848 | 2200 |

FIG. 5

```
┌─────────────────────────────────────────────────────────────┐
│ Combine purified water with a compound mixture, the compound mixture │
│ being non-reactive with the water and a conductor of an electric field and a │
│ magnetic field 1302                                         │
└─────────────────────────────────────────────────────────────┘
                              │
                              ▼
┌─────────────────────────────────────────────────────────────┐
│ Apply the magnetic field and the electric field to the combination of the │
│ purified water and the compound mixture to cause generation of the │
│ structurally altered gas molecules, the structurally altered gas molecules │
│ having a higher probability of attraction of electrons into areas adjunct to the │
│ structurally altered gas molecules than molecules of the purified water 1304 │
└─────────────────────────────────────────────────────────────┘
                              │
                              ▼
┌─────────────────────────────────────────────────────────────┐
│ Introduce the structurally altered gas molecules into an environment of a │
│ chemical process, wherein the structurally altered gas molecules facilitate │
│ electron transfers during the chemical process, thereby increasing output of │
│ the chemical process 1306                                   │
└─────────────────────────────────────────────────────────────┘
```

GENERATION OF STRUCTURALLY ALTERED GAS MOLECULES FROM WATER AND APPLICATION THEREOF

CROSS-REFERENCE TO RELATED APPLICATIONS

This application is a divisional application of U.S. application Ser. No. 18/376,790 filed on Oct. 4, 2023, and entitled "GENERATION OF STRUCTURALLY ALTERED GAS MOLECULES FROM WATER AND APPLICATION THEREOF," which in turn is a Continuation-in-Part of PCT Application No. PCT/US22/44167 filed on Sep. 21, 2022, and entitled "STRUCTURALLY ALTERED GAS MOLECULE PRODUCED FROM WATER AND METHOD OF GENERATION THEREOF," which claims benefit of and priority of U.S. patent application Ser. No. 17/487,613 filed on Sep. 28, 2021, and entitled "STRUCTURALLY ALTERED GAS MOLECULE PRODUCED FROM WATER AND METHOD OF GENERATION THEREOF." U.S. application Ser. No. 18/376,790 is a Continuation-in-Part of PCT Application No. PCT/US22/44168 filed on Sep. 21, 2022, and entitled "STRUCTURALLY ALTERED GAS MOLECULE PRODUCED FROM WATER AND METHOD OF GENERATION THEREOF," which claims benefit of and priority of U.S. patent application Ser. No. 17/487,613 filed on Sep. 28, 2021, and entitled "STRUCTURALLY ALTERED GAS MOLECULE PRODUCED FROM WATER AND METHOD OF GENERATION THEREOF," and claims benefit of and priority of U.S. patent application Ser. No. 17/743,632 filed on May 13, 2022, and entitled "STRUCTURALLY ALTERED GAS MOLECULE PRODUCED FROM WATER AND METHOD OF GENERATION THEREOF." The subject matter of the aforementioned applications is incorporated herein by reference in its entirety.

TECHNICAL FIELD

This disclosure relates to methods for generation and deployment of a structurally altered gas molecules derived from water.

BACKGROUND

Gas infusion is a widely employed technique for modifying and enhancing the characteristics of liquids. Gas-infused liquids are used in altering pH levels, oxidation/reduction potentials, and so forth and serve diverse purposes, including facilitating polymerization, promoting salt formation, inducing crystallization, and others. Furthermore, the resulting gas molecules can serve as clean fuel. When incorporated into other fuels, these gas molecules prove valuable in improving power generation, enhancing efficiency, and reducing emissions. Additionally, these gas molecules offer a range of health benefits to various forms of wildlife and plant life, while also contributing to the enhancement of manufacturing processes and the application of manufactured products.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

According to one example embodiment of the present disclosure, a method for generation and deployment of a structurally altered gas molecules derived from water. The method may include combining purified water with a compound mixture. The compound mixture is non-reactive with the water and a conductor of an electric field and a magnetic field. The method may include applying the magnetic field and the electric field to the combination of the purified water and the compound mixture to cause generation of the structurally altered gas molecules. The structurally altered gas molecules have a higher probability of attraction of electrons into areas adjunct to the structurally altered gas molecules than molecules of the purified water. The method may further include introducing the structurally altered gas molecules into an environment of a chemical process. The structurally altered gas molecules facilitate electron transfers during the chemical process, thereby increasing output of the chemical process.

According to another embodiment of the present disclosure, a system for generation and deployment of a structurally altered gas molecules from water is provided. The system may include a first container for combining purified water with a compound mixture. The compound mixture may be non-reactive with the water and a conductor for an electric field and a magnetic field. The system may include a magnetic field generator and an electric field generator designed to apply the magnetic field and the electric field to the combination of the purified water and the compound mixture to cause generation of the structurally altered gas molecules. The structurally altered gas molecules have a higher probability of attraction of electrons into areas adjunct to the structurally altered gas molecules than molecules of the purified water. The system may include a second container for introducing the structurally altered gas molecules into an environment of a chemical process. The structurally altered gas molecules facilitate electron transfers during the chemical process, thereby increasing output of the chemical process.

Other example embodiments of the disclosure and aspects will become apparent from the following description taken in conjunction with the following drawings.

BRIEF DESCRIPTION OF DRAWINGS

Exemplary embodiments are illustrated by way of example and not limitation in the figures of the accompanying drawings, in which like references indicate similar elements.

FIG. 4 illustrates characteristics of the gas according to the present disclosure.

FIG. 5 illustrates characteristics of the gas according to the present disclosure.

FIG. 13 is a flow chart of a method for generation and deployment of a structurally altered gas molecules derived from water, according to an example embodiment.

DETAILED DESCRIPTION

Figure 1:
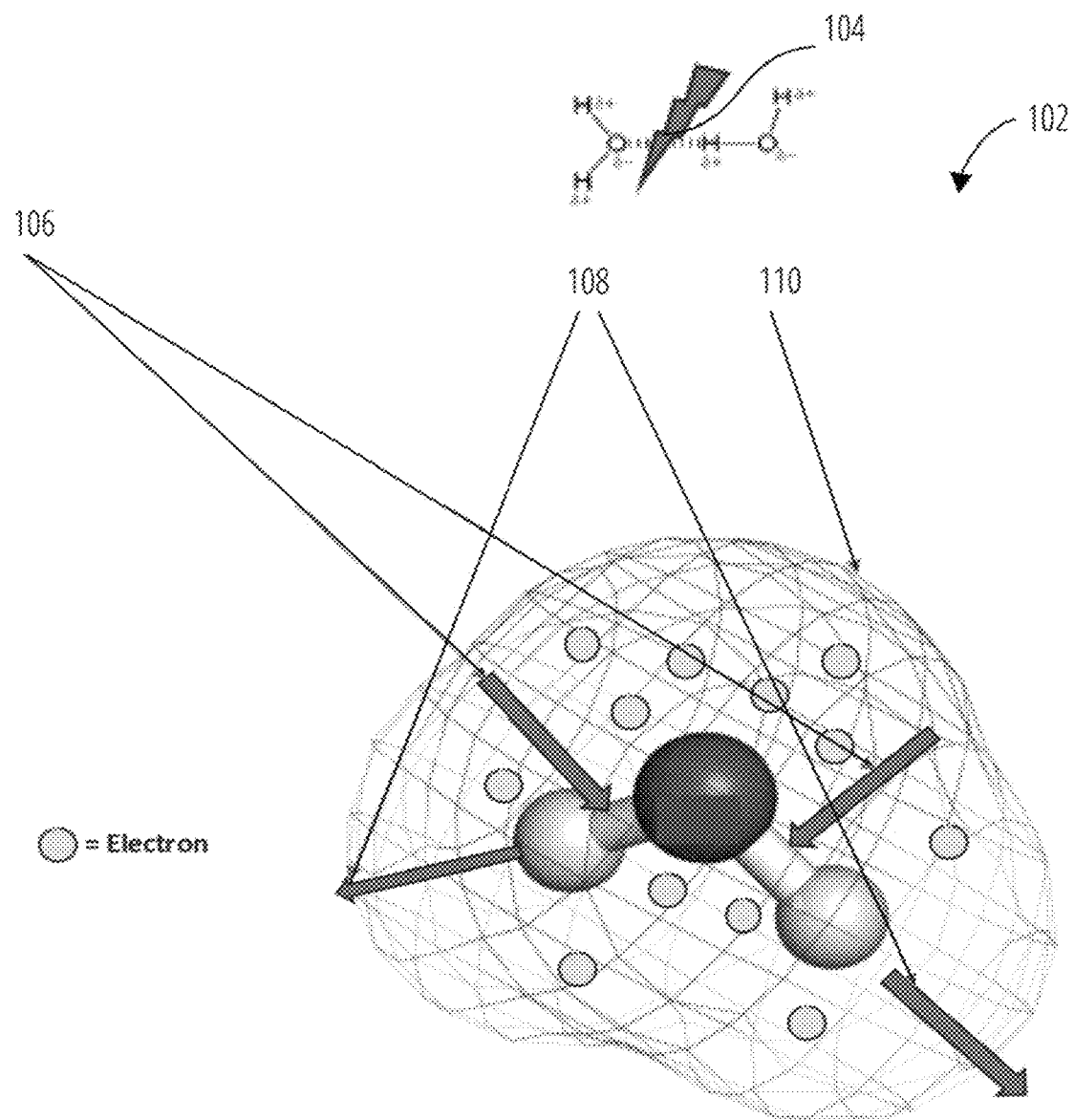
FIG. 1 shows a structurally altered gas molecule deployed in the method for generation and deployment of a structurally altered gas molecules derived from water, according to an example embodiment.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and operational changes can be made without departing from the scope of what is claimed. The following detailed description is, therefore, not to be taken in a limiting sense, and the scope is defined by the appended claims and their equivalents.

Generally, the embodiments of this disclosure relate to methods for generation and deployment of a structurally altered gas molecules derived from water. The generation of the structurally altered gas molecules is performed in a chemical reaction chamber that may accommodate compound mixtures in a solid, liquid, gas, or multi-phase form. The chemical reaction chamber may have a specific geometric electromagnetic field configuration to attract hydrated and/or conventional electrons into the adjacent areas of the water molecules without a chemical reaction occurring between the water molecules.

The method according to the present disclosure results in creating a water molecule with special characteristics by treatment of water into the chemical reaction chamber. The chemical reaction chamber may be characterized by two configurations. First, the chemical reaction chamber enables the introduction of a compound mixture, which may be in solid, liquid, gas, or multi-phase form, the purpose of which is to support or enhance electromagnetic field and which specifically does not have any chemical interaction with the water. Second, the chemical reaction chamber enables the introduction of energy in a geometrically configured manner, in which the result of the treatment of the water molecules is to render the water molecule to have a greater probability to attract hydrated and/or conventional electrons into the adjacent areas of the water molecules, without a chemical reaction between the water molecule and the electrons.

In the chemical reaction chamber, for a period after the treatment of the water molecules, the electron attracting water molecules can be introduced to an environment, in which a separate chemical, non-chemical, or hybrid process is occurring and in which heightened hydrated and/or conventional electron availability (either accepting or donating) may be useful in allowing and/or enhancing the productivity of such process. Either organically, such as the water molecule's advantage in electron transport in the mitochondria or in various inorganic processes, such as, for example, the production of hydrogen or the reduction of carbon dioxide equivalents ($CO_2e$).

The method according to the present disclosure involves the introduction of a compound mixture, which may be in solid, liquid, gas, or multi-phase form, the purpose of which is to support or enhance electromagnetic field and which specifically does not have any chemical interaction with the water. The gas including the structurally altered gas molecules can be deployed directly into a plurality of processes that use electrons and the molecule itself for any process that requires them. The applications of the method according to the present disclosure may include but are not limited to fossil fuel and energy processes, fossil hydrogen turbines, hydrogen fuel and energy processes, hydrogen engines and hydrogen fuel cells to generate power, adenosine triphosphate (ATP) production, increase efficiency and reduce $CO_2e$ emissions to the environment from these and other hydrogen combustion systems, agriculture applications, all forms of water treatment including desalinization, contaminant removal such as polymeric compounds (e.g., per- and polyfluoroalkyl (PFA) compounds), and the like, both organic and inorganic.

The structurally altered gas molecules may be diffused into normal pure water where it has been demonstrated that the structurally altered gas molecules impart their properties to the un-gassed normal pure water. The restructuring of normal water molecules by diffusion of the structurally altered gas molecules into it has shown the following observed alterations in the gas diffused water allowing the accommodation of excess electrons. The first alteration is reduction in intermolecular hydrogen bonding between water molecules in liquid phase. Hydrogen bonding in water is a dynamic attraction between positively charged hydrogen atoms of one water molecule and negatively charged oxygen atoms of another water molecule. This occurs because of the difference in electronegativity between hydrogen and oxygen atoms. The second alteration is reduction in the dipole moment of the gas treated water. The dipole moment is a measure of the separation of positive and negative electrical charges within a system. Water has a dipole moment because water has a bent structure and the electronegativity difference between atoms of oxygen and hydrogen. The third alteration is reduction in the ion-dipole force formed between ions and water. The ion-dipole force is a force of attraction between an ion and a neutral molecule that has a dipole. Moreover, the generation of the structurally altered gas molecules results in formation of hydrated electrons from the surplus excess electrons provided by the infusion of the structurally altered gas molecules.

These alterations reduce the tendency of the water molecules to "clump" through hydrogen bonding, and its dipole moment. The alterations also provide a reduction in the ion-dipole force formed between ions and water to facilitate the separation and passage of individual water molecules through ion water separation technologies used in the separation of ions (both soluble and insoluble) from process fluids and in the purification of water. With these changes provided by the method according to the present disclosure, the desirable effects on the chemical kinetics (speed of reaction) and thermodynamics (how far to completion the reactions may go) have been demonstrated. Passage of individual water molecules through water treatment processes, separation technologies and membranes used for purification of water by altering the ion-ion, ion-water, and water-water interactions in solution have been demonstrated and documented in experiments. Results from the experiments conclude a significant reduction in water and energy consumption and increased sustainability benefit when using the method according to the present disclosure in brackish/ seawater reverse osmosis desalinization applications. In one of the experiments, efficiency improvements of 25% in salt removal efficiency have been documented with all other consumables being equal.

The method according to the present disclosure uses conventional water treatment technologies to generate a purified liquid. That liquid is added to a chemical reaction chamber that contains an electrolyte, which may be in solid, liquid, or gaseous form, or a combination of the above. This mixture is subjected to a focused magnetic field using a magnetic field generator and an electric field to generate an altered, gaseous form of said purified liquid. The generated altered water molecule gas can then be deployed directly into the desired application. In an example embodiment, the magnetic field generator may include one of the following: earth magnets, solenoids, electromagnets, and so forth.

The structurally altered gas molecule has been tested in a plurality of tests. The tests illustrate the example embodiments of the present disclosure.

Components involved in a method described in the present disclosure include water, water pretreatment equipment, a chemical reaction chamber (can contain solid, liquid, or gas compound mixtures, or combination of all), an electrolyte solution, a magnetic field generator, and electricity. Additional components may include pressure regulators, an electrical inverter, solar panels, and a gas diffuser for diffusing gas into atmosphere or liquid that living cells can interface with and uptake the altered water molecule in gaseous and/or liquid form.

Water serves as the raw material that the gas product is generated from. Water pretreatment equipment is used to prepare the water for the reaction chamber using such steps as conventional filtration, absorption, and purification. The reaction chamber provides the reaction vessel that holds the solid, liquid, or gas compound mixtures, or combination of all and the purified water for the magnetic field to chemically convert the purified water into an altered gaseous form of the purified liquid. The chemical reaction chamber provides the medium for the magnetic field to align and impart its energy on the purified water mixed in the chemical reaction chamber to chemically generate the altered gaseous form of the water. The magnetic field generator, e.g., in the form of earth magnets, creates magnetic field to drive the chemical reaction that generates the altered form of the gaseous water. Once generated, the gas can be deployed directly into the desired application. For example, the gas, i.e., structurally altered gas molecules, can be deployed directly into public and private influent water, industrial process water and waste water streams to enhance the performance of the existing technology and in some cases eliminate the need for existing sub-components and their corresponding capital and operational costs. The gas according to the present disclosure (hereinafter referred to as a gas) contains the surplus electrons and hydrated electrons. The method according to the present disclosure weakens the affinity of the water molecules around the hydrated electron giving the hydrated electron access to the carbon-fluorine (C—F) bonds in polymeric substances, such as per- and polyfluoroalkyl substances (PFAS), and degrading the polymeric substances such as PFAS to non-harmful compounds.

Thus, the method of the present disclosure includes treating water in the chemical reaction chamber with an electromagnetic field while introducing energy into the chemical reaction chamber based on predetermined parameters (e.g., temperature, pressure, time, and so forth). This results in breaking hydrogen bonds and eventual change in physical properties of the water molecules, i.e., structurally altered gas molecules which behave differently from water. Upon generation of the structurally altered gas molecules, the structurally altered gas molecules are introduced into a water container where the structurally altered gas molecules interact with molecules of water and impart the behavior of the structurally altered gas molecules to the molecules of water. Specifically, some hydrogen bonds in the molecules of water break, i.e., they become similar to the hydrogen bonds in the structurally altered gas molecules. Thus, the structurally altered gas molecules, when infused in water, are able to influence the structure of the molecules of water and, hence, provide some of their properties to the molecules of water. The resulting amount of structurally altered gas molecules (i.e., the structurally altered gas molecules and the molecules of water changed by the structurally altered gas molecules) may facilitate electron transfers when introduced into a chemical process.

The liquid form of the structurally altered gas molecules infused in water may serve as a storage system for the structurally altered gas molecules because the structurally altered gas molecules maintain their properties in the liquid form. The structurally altered gas molecules from the storage system can be used in a chemical process at later time.

Referring now to the drawings, various embodiments are described in which like reference numerals represent like parts and assemblies throughout the several views. It should be noted that the reference to various embodiments does not limit the scope of the claims attached hereto. Additionally, any examples outlined in this specification are not intended to be limiting and merely set forth some of the many possible embodiments for the appended claims.

This application claims priority of U.S. patent application Ser. No. 17/487,613, filed on Sep. 28, 2021 and U.S. patent application Ser. No. 17/743,632, filed on May 13, 2022, now U.S. Pat. No. 11,634,823, the subject matter of which is incorporated herein by reference in its entirety for all purposes. Processes and systems described herein may be better understood in light of the concepts found in these references.

FIG. 1 shows a structurally altered gas molecule 102 deployed in the method for generation and deployment of a structurally altered gas molecules derived from water. The structurally altered gas molecule deployed in the method according to the present disclosure may include a structurally altered gas molecule generated by processes described in U.S. Pat. Nos. 11,384,440 and 11,634,823.

During the alterations, hydrogen bonds 104 are broken to allow a gaseous single molecule form of water to exist and enable the following adjustments: 1) a bond angle 106 is decreased; 2) oxygen-hydrogen covalent bond length 108 is increased; 3) adjustments allow room for more electrons in probability spheres 110. Per the molecular orbital theory (MOT), small molecules like water can adjust electron energy levels around the probability spheres. The MOT states that not just the atoms themselves but the entire molecule shares electrons.

As to the structurally altered gas molecule 102, the molecular alterations include lengthening of the H—O bonds from 0.95 Angstroms up to 1.3 Angstrom and decreasing the H—O—H bond angle from 104.5° to as small as 94°. These changes alter the chemical properties of the water that the gas may be infused into. These changes include a decrease in normal pure water pH (from 7.0 to ~6.5), and a shift in redox potential from 0 mV to ~−200 mV. This gas has been diffused into normal pure water where it has been demonstrated that the infused gas imparts some of its above-described properties to the un-gassed normal pure water.

The gas, i.e., structurally altered gas molecules, has been diffused into normal pure water where it has been demonstrated that the gas imparts its above-described properties to the un-gassed normal pure water.

Figure 2:
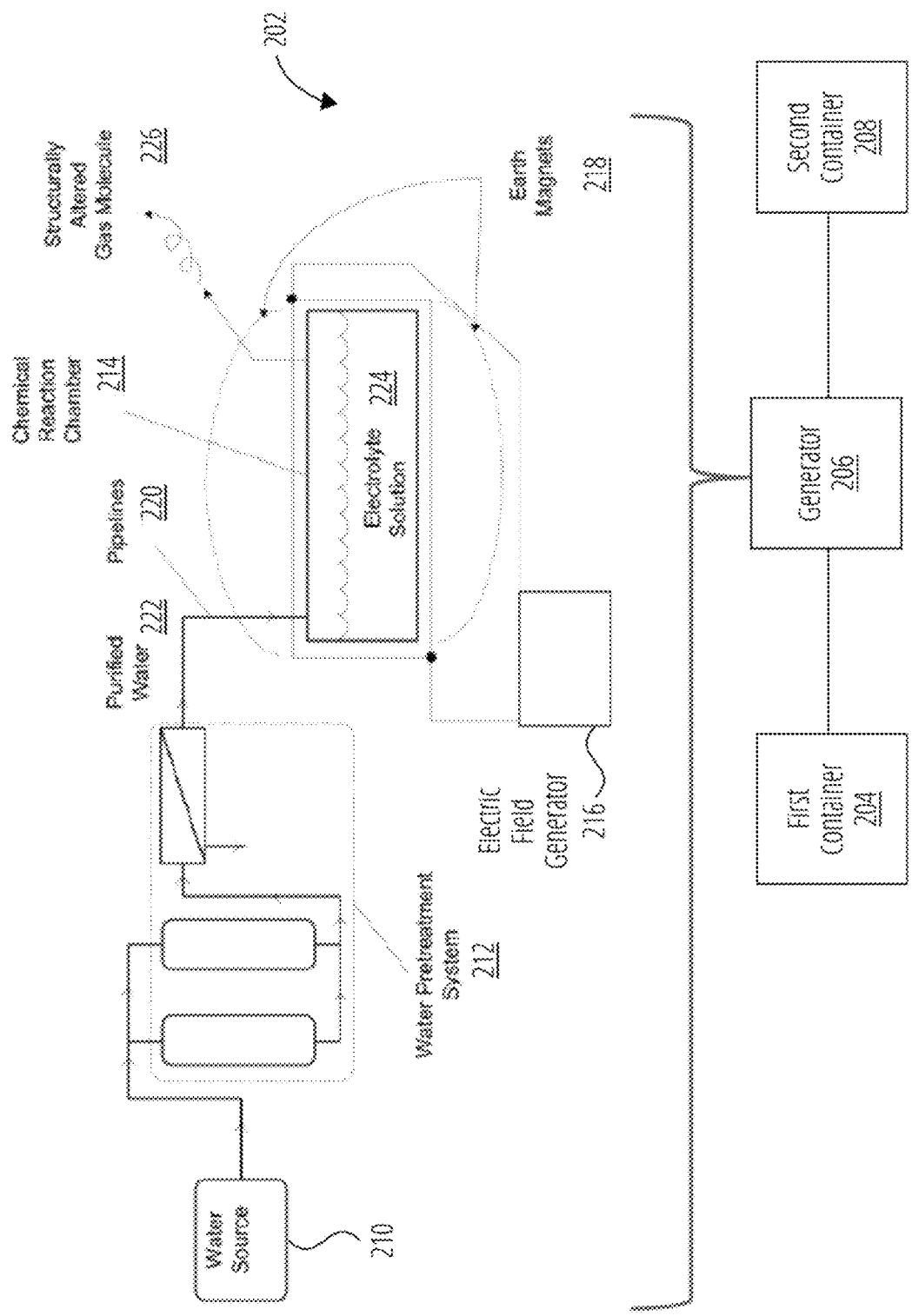
FIG. 2 is a diagram showing a system for generation and deployment of a structurally altered gas molecules derived from water, according to an example embodiment.

FIG. 2 is a diagram showing a system 202 for generation and deployment of a structurally altered gas molecules derived from water, according to an example embodiment. The system 202 may include a first container 204, a generator 206, and a second container 208.

The first container 204 may be configured to combining purified water with a compound mixture. The compound mixture may be non-reactive with the water and a conductor for an electric field and a magnetic field.

The generator 206 may include a magnetic field generator and an electric field generator 216. In an example embodiment, the magnetic field generator is implemented in the form of earth magnets 218. The magnetic field generator and the electric field generator 216 may be designed to apply the magnetic field and the electric field to the combination of the purified water and the compound mixture to cause generation of the structurally altered gas molecules. The structurally altered gas molecules have a higher probability of attraction of electrons into areas adjunct to the structurally altered gas molecules than molecules of the purified water.

The second container 208 may be configured to introduce the structurally altered gas molecules into an environment of a chemical process. The structurally altered gas molecules facilitate electron transfers during the chemical process, thereby increasing output of the chemical process.

The generator 206 is an example system for generating a structurally altered gas molecule, according to an example embodiment. The generator 206 may include a water source 210, a water pretreatment system 212, a chemical reaction chamber 214, the electric field generator 216, a magnetic field generator, e.g., the earth magnets 218, and pipelines 220. The generator 206 may also include pressure regulators. The electric field generator 216 may include an electrical inverter and solar panels.

The water source 210 may provide water as a raw material for generating the gas molecule product. The water pretreatment system 212 may prepare the water for the chemical reaction chamber 214. The water pretreatment system 212 may include a filtration system, an absorption system, and a purification system to produce the purified water 222.

The chemical reaction chamber 214 may be configured to accommodate water and may contain an electrolyte solution 224. The electrolyte solution 224 can be made using a mixture of a hydroxide salt and an acid salt. The purified water 222 can be provided to the chemical reaction chamber 214. The earth magnets 218 may generate a permanent focused magnetic field. The electric field generator 216 may generate an electric field. The focused magnetic field and the electrical field may drive a chemical reaction that generates the structurally altered gas molecule 226 from the purified water supplied into the chemical reaction chamber 214. The electrolyte solution 224 may provide a medium for the focused magnetic field to align and impart energy of the focused magnetic field on the purified water mixed in with the electrolyte solution and, thereby, chemically generate the structurally altered gas molecule 226 from the purified water 222. The temperature in the chemical reaction chamber 214 can be from 60 degrees to 120 degrees Fahrenheit. The pressure in the chemical reaction chamber 214 can be from 1 atmosphere to 40 pounds per square inch gauge (psig). The structurally altered gas molecule 226 may have a higher probability of attraction of electrons into areas adjunct to the structurally altered gas molecule 226 than molecules of the water.

The structurally altered gas molecule 226 can be 99.9% hydrogen and oxygen combination in two parts of hydrogen to one part of oxygen ratio at the Standard Temperature of 68 degrees of Fahrenheit and Pressure of 1 atmosphere (STP). The structurally altered gas molecule 226 may have the O—H bond length between 0.95 and 1.3 angstroms and the H—O—H bond angle between 94 degrees and 104 degrees.

The molecular weight of the structurally altered gas molecule 226 can be between 12.14 and 12.18 atomic mass units (AMUs) at STP. In comparison, the molecular weight of pure water vapor is 18 AMUs at STP. At STP, the relative density of the structurally altered gas molecule 226 compared to dry air is 41.18%-42.00%. In comparison, relative density of pure water vapor compared to dry air is 62.19%. The structurally altered gas molecule 226 may remain stable at pressure more than 300 psig.

When dissolved in pure water having 2 parts per million (ppm) of total dissolved solids (TDS) at 25 degrees of Celsius, the structurally altered gas molecule 226 may generate an oxidation reduction potential (ORP) of approximately −50 to −360 mV and a pH of 6.1 to 6.8 in the resulting gas-water mixture. The ORP and pH may remain stable in a closed insoluble vessel for at least 30 days. In comparison, the pure water does not possess a stable negative ORP at a pH below 7.

When dissolved in pure water (2 ppm TDS at 25 degrees Celsius), the structurally altered gas molecule 226 may reduce the concentration of TDS from 2.0 ppm to 1.0 ppm, i.e., the reduction is 50%. Barring contamination, the concentration of TDS remains stable at 1 ppm in a closed insoluble vessel indefinitely.

The changes in structure and properties of the structurally altered gas molecule 226 are caused by changes in electronic structure of the gas structurally altered structurally altered gas molecule 226 due to applying the focused magnetic field and the electrical field to the mixture of the electrolyte solution 224 and purified water 222.

In an example embodiment, a structurally altered gas molecule 226 used in the method for generation and deployment of a structurally altered gas molecules derived from water is a combination of two parts of hydrogen and one part of oxygen and produced from water. The structurally altered gas molecule 226 is produced by placing an electrolyte solution in a chemical reaction chamber, adding purified water to the chemical reaction chamber, and applying a focused magnetic field generated by a magnetic field generator and an electric field to a mixture of the purified water and the electrolyte solution to cause generation of the structurally altered gas molecule from the purified water. The temperature in the chemical reaction chamber may be from 60 degrees to 120 degrees Fahrenheit. The pressure in the chemical reaction chamber may be from 1 atmosphere to 40 psig. The structurally altered gas molecule 226 has a hydrogen-oxygen-hydrogen bond angles between 94 degrees and 104 degrees and hydrogen-oxygen bond length between 0.95 Angstrom and 1.3 Angstrom. A hydrogen bonding of the structurally altered gas molecule 226 is neutralized. The structurally altered gas molecule 226, when being dissolved in water, may have two parts per million (ppm) of TDS, causing the TDS to reduce to one ppm. When being dissolved in the purified water, the structurally altered gas molecule 226 and the water may form a solution having a pH ranging from 6.1 to 6.8.

The structurally altered gas molecule 226 may be produced with a mixture of a hydroxide salt and an acid salt as the electrolyte. The structurally altered gas molecule 226 may have a density relative to a dry air of from 41.18% to 42%. The structurally altered gas molecule 226 may be stable at a pressure exceeding 300 psig. The structurally altered gas molecule 226 may have a peak at 600 inverse centimeters in an infrared spectrum.

In an example embodiment, upon dissolving the structurally altered gas molecule 226 in water, a solution of the structurally altered gas molecule 226 and water is produced. The solution may have an oxidation/reduction potential of −50 to −360 millivolts and pH from 6.1 to 6.8. The oxidation/reduction potential and the pH may remain stable for at least 30 days after the solution is placed in a closed insoluble vessel. When infused in water, the structurally altered gas molecule 226 may cause a hydrogen bonding in the water to be neutralized.

In an example embodiment, the structurally altered gas molecules may be used in generation of energy alternative to hydrogen energy. The gas according to the present disclosure, i.e., the structurally altered gas molecules, provides 21.2% more energy in kJ/kg generated. At present, green hydrogen costs $1-$2 dollars per kilogram to manufacture. Blue hydrogen is $5-$7 per kilogram. The gas according to the present disclosure is $0.658 per kilogram. The gas according to the present disclosure requires no oxygen stripping process like grey, brown, green, blue hydrogen. The method according to the present disclosure generates NO $NO_X$, $SO_X$, or $CO_2e$. Nearly 100% of the burned fuel is capture and rejuvenated in the system 202 compared to a conventional hydrogen burning system where the exhaust products are not captured and which are less efficient. The gas, according to the present disclosure, can be stored and transported or generated on board and used real-time. The gas according to the present disclosure provides no toxic exposure to operators or users. There are no toxins generated with the method according to the present disclosure. The raw materials for the gas (water) are collected and recycled indefinitely. Footprint for 100 MW plant for performing the method according to the present disclosure is 0.0098 sq km or 0.004 sq mi. Footprint for 100 MW hydrogen plant is 3× or more. Footprint for 100 MW wind farm is 25 sq km or 10 sq mile. Footprint for 100 MW solar panel field is 25 sq km or 10 sq mile.

Figure 3:
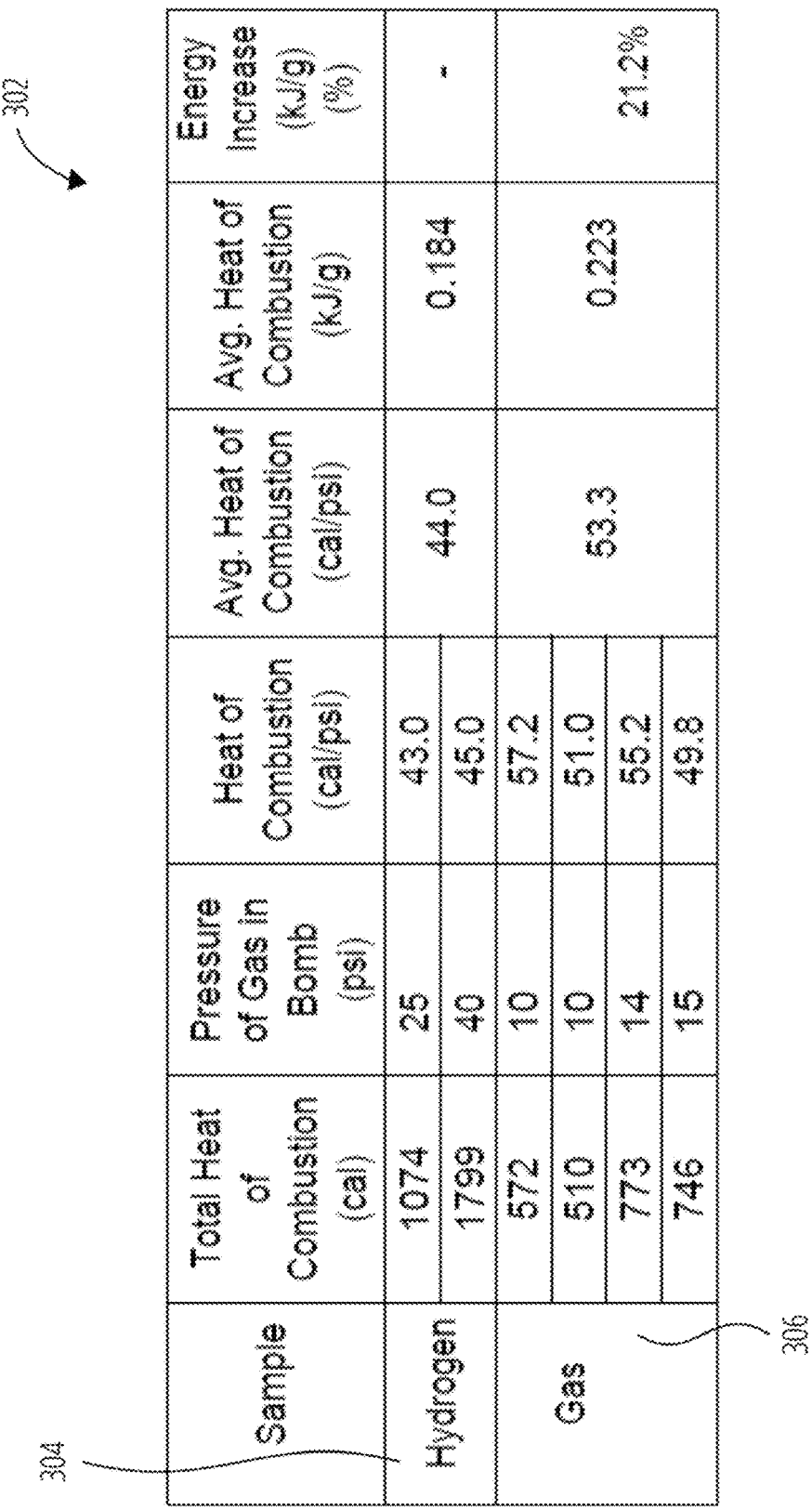
FIG. 3 shows a table illustrating calorimetry test results obtained in a bomb calorimetry experiment, according to an example embodiment.

FIG. 3 shows table 302 illustrating calorimetry test results obtained in a bomb calorimetry experiment to confirm higher energy in kJ per kg. The heat of combustion was measured using a modified American Society for Testing and Materials (ASTM) D240 procedure which enables the combustion of gasses rather than of liquids or solids as is normally the case. For hydrogen 304, oxygen was supplied in stoichiometric excess. For the gas 306 of the present disclosure, no additional oxygen or air was supplied. In each test, the vessel was filled with sample gas twice, released to remove any residual air, and refilled a third time.

FIG. 4 and FIG. 5 illustrate characteristics of the gas according to the present disclosure. FIG. 4 is a table 402 illustrating results of the standard ASTM D 1945 test for analysis of the gas according to the present disclosure by gas chromatography.

FIG. 5 is a table 502 illustrating characteristics of natural gas 504, hydrogen 506, and gas 508 of the present disclosure.

The structurally altered gas molecule is a molecule consisting of hydrogen and oxygen in a 2:1 ratio. It is not a mixture of $H_2$ and $O_2$ gases and not hydrogen peroxide or conventional pure water or water vapor. The structurally altered gas molecule exists as a gas at standard temperature that can be pressured up to 300 psig, while maintaining its stability. The structurally altered gas molecule has no geographic limitations for production. Unlike hydrogen, the structurally altered gas molecule does not back propagate, however, like for all fuels a certain pressure has to be maintained. The structurally altered gas molecule can be generated as it is used or can be stored like other gasses used in combustion turbines. The structurally altered gas molecule creates a flame when it burns and does not create explosion like hydrogen. Generation of the structurally altered gas molecules is scalable, sustainable, and safe.

Figure 6:
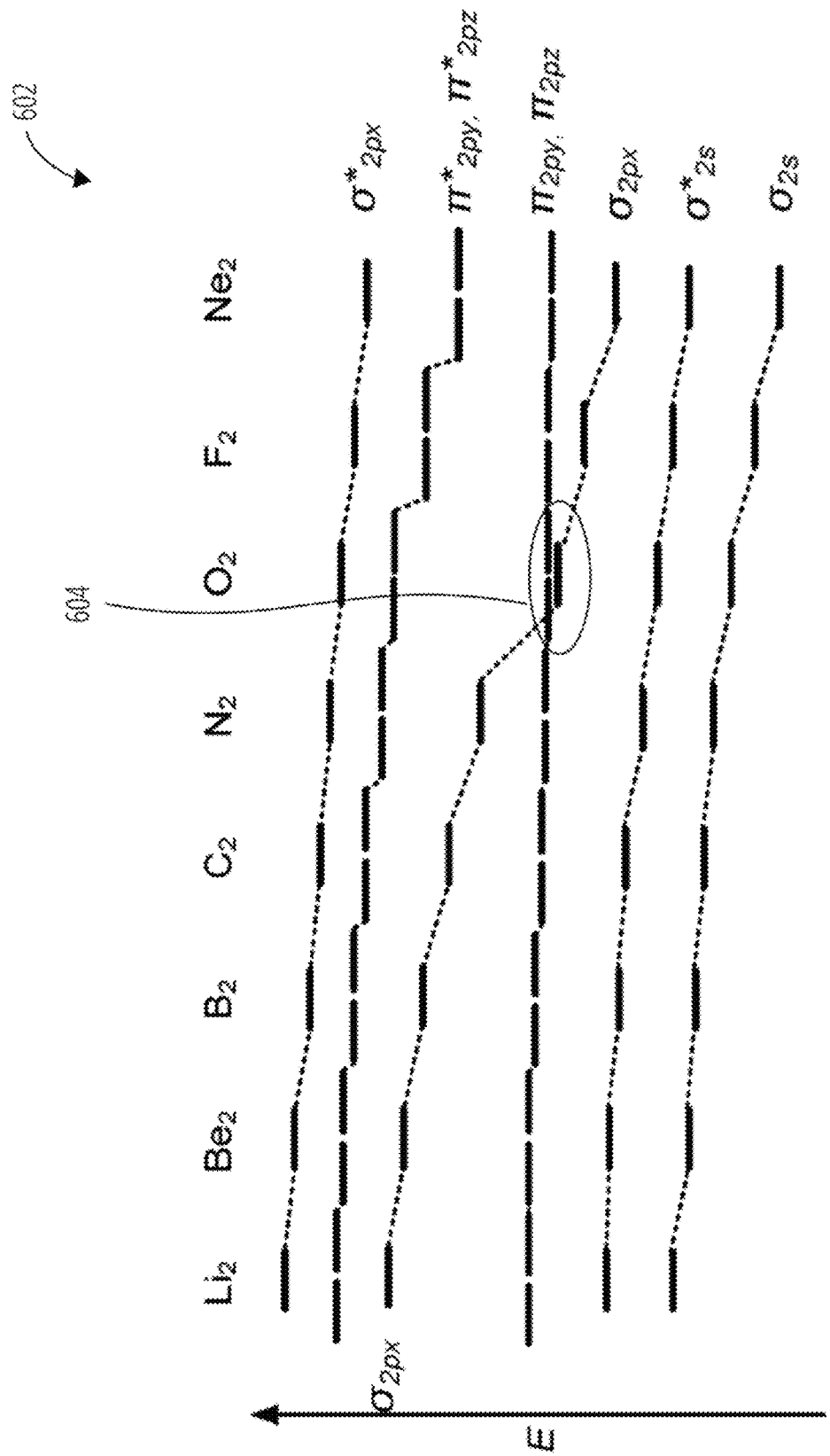
FIG. 6 is a diagram showing energy levels of molecular orbitals of homonuclear diatomic molecules of elements of the second period in the periodic table.

FIG. 6 is a diagram showing energy levels 602 of molecular orbitals of homonuclear diatomic molecules of elements of the second period in the periodic table. The gas according to the present disclosure has structural differences compared to divalent hydrogen, divalent oxygen, and pure water. The structural changes made to the gas according to the present disclosure include changes in the bond angle, bond length, and neutralization of the hydrogen bonding found in regular water. This is accomplished by imparting sufficient focused energy on regular water to overcome the collective bond energies mentioned above. Structural changes to allow molecules of the same outer valence orbitals with lone pairs of electrons in their structure (for example water) allow certain normally "liquid" molecules to exist as gasses and at standard temperature and pressure after these said structural changes. These structural changes are observed in nature, and the phenomena is supported by MOT.

In MOT, there is known a phenomenon called σ-π (sigma-pi) mixing. This phenomenon influences existing s and p molecular orbitals by imparting electromagnetic energy at the molecular level. In the case of oxygen, the sigma-2px, pi-2py and pi-2pz orbitals 604 are close enough to alter the respective stability at the molecular level. Thus, the energy levels of these orbitals can supersede each other with only small amounts of focused energy input. This superseding in the energy levels has a direct effect on the molecular wave function of a molecule, effective nuclear charge, atomic radius, and causes significant changes in the molecular structure.

Figure 7:
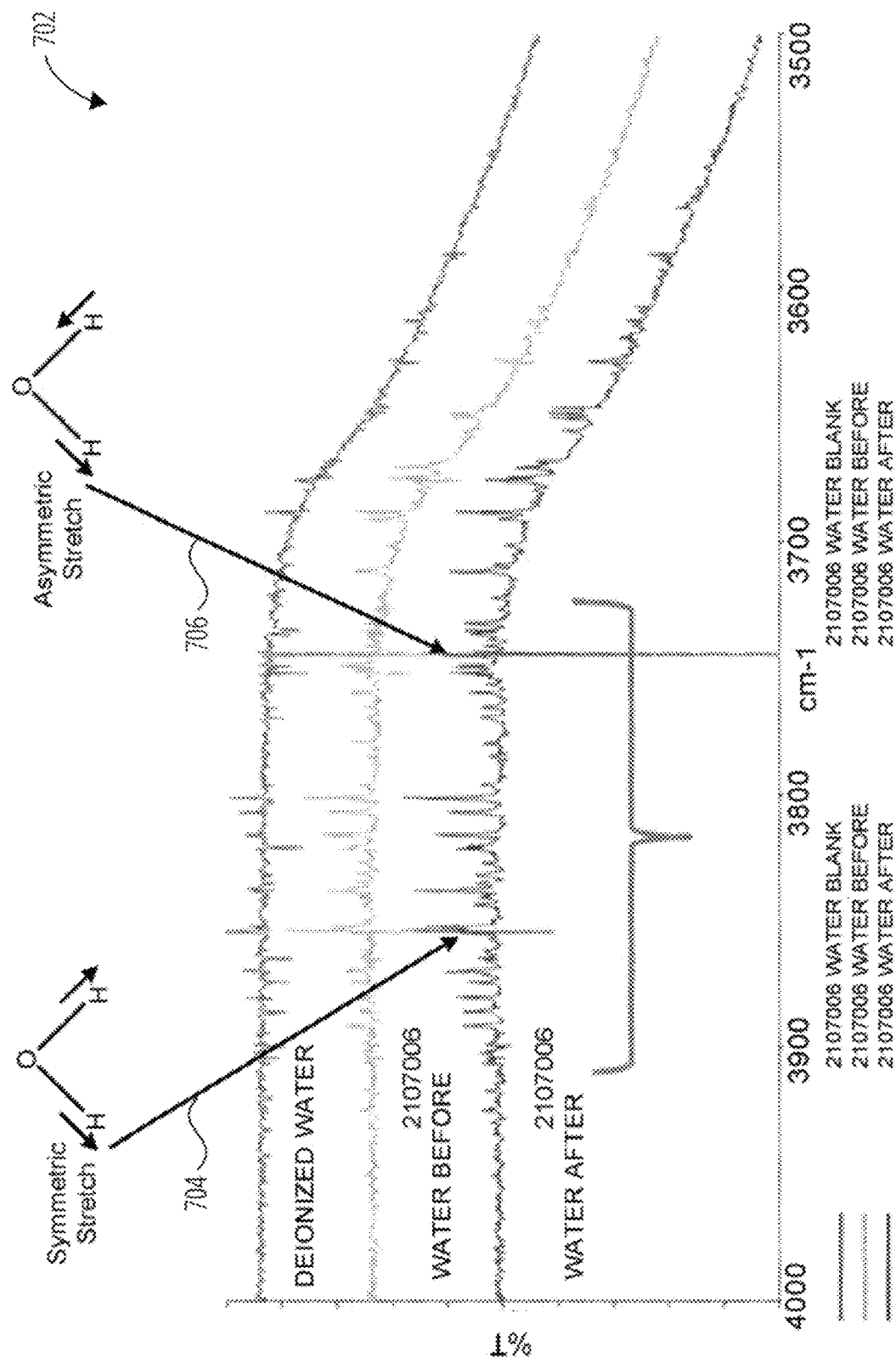
FIG. 7 is a plot of the Fourier Transform Infrared transmittance spectra of deionized water, a pure water before infusion with the structurally altered gas molecule, and a pure water after infusion with the structurally altered gas molecule, according to an example embodiment.

FIG. 7 is a plot 702 of the Fourier Transform Infrared (FTIR) transmittance spectra of deionized water, a pure water before (WB) infusion with the structurally altered gas molecule, and a pure water after (WA) infusion with the structurally altered gas molecule in the region of 3500-4000 inverse centimeters ($cm^{-1}$).

Figure 8:
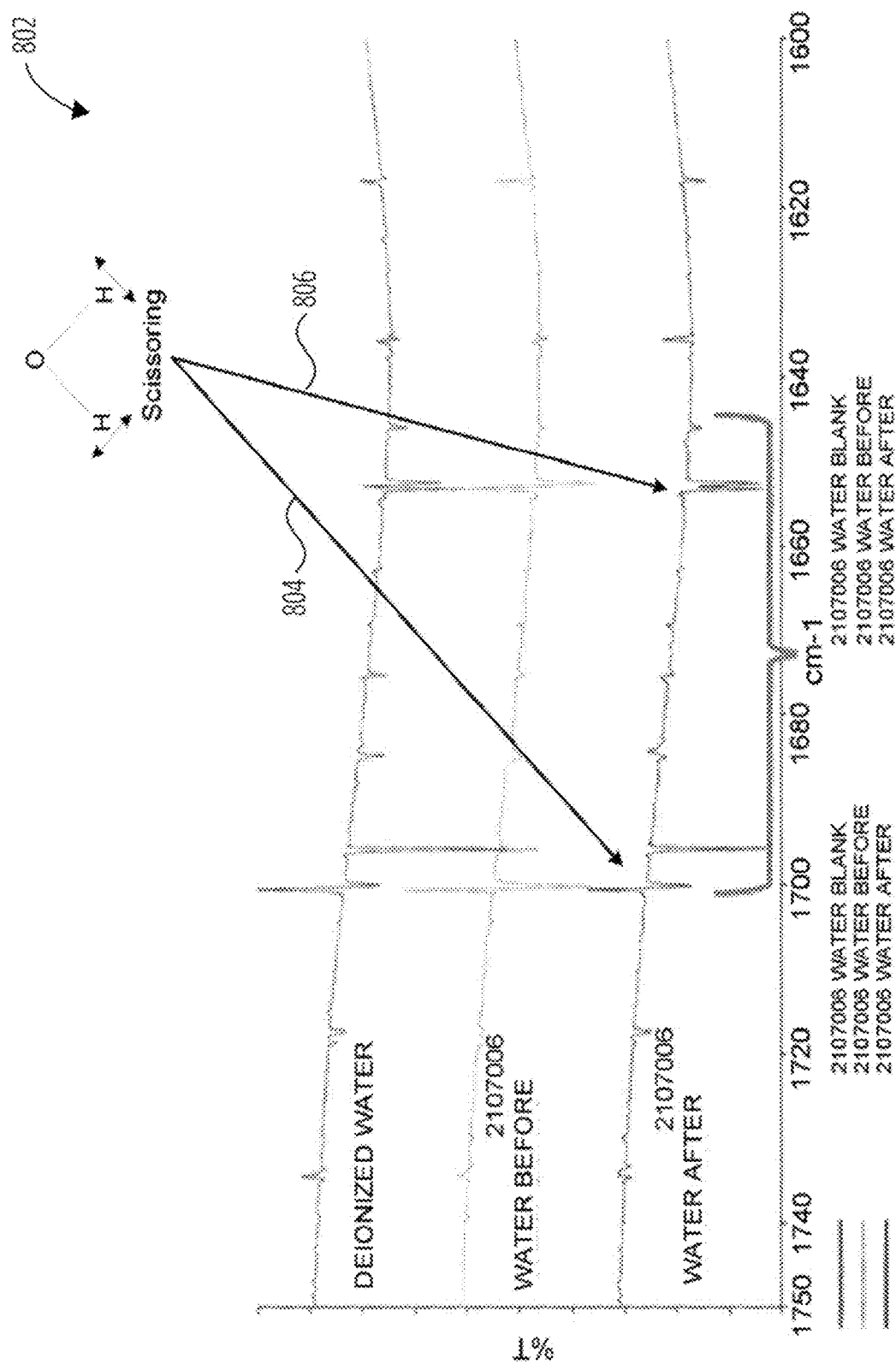
FIG. 8 is a plot of the Fourier Transform Infrared transmittance spectra of deionized water, a pure water before infusion with the structurally altered gas molecule, and a pure water after infusion with the structurally altered gas molecule, according to an example embodiment.

FIG. 8 is a plot 802 of the FTIR transmittance spectra of deionized water, WB, and WA in the region of 1600-1750 $cm^{-1}$. The plot 702 and plot 802 show differences in bands corresponding to the symmetrical and asymmetrical stretch in bond length and bands corresponding to the bond angle "scissoring".

FIG. 7 and FIG. 8 show the actual structural changes to the water molecule's bond length Stretch) and bond angle resulting from treatment by the gas according to the present disclosure. See changes referenced by arrows 704 and arrows 706 in FIG. 7 and arrows 804 and arrows 806 in FIG. 8 toward the changes in downward "dips" at specific transmittance (% T) and time interval ($cm^{-1}$).

Figure 9:
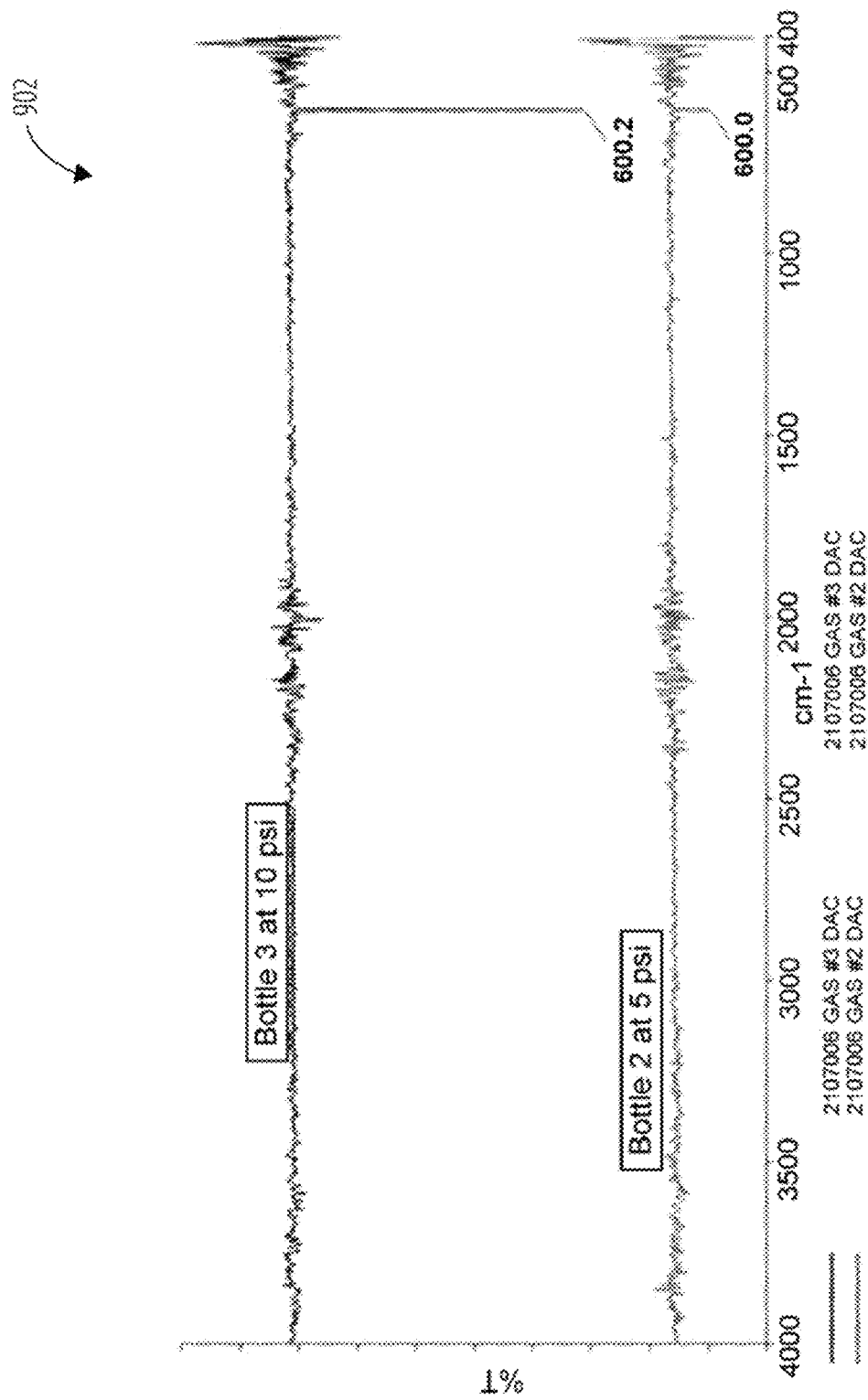
FIG. 9 shows plots of Fourier Transform Infrared molecular spectra of the structurally altered gas molecule, according to an example embodiment.

FIG. 9 shows plots 902 of FTIR molecular spectra of the structurally altered gas molecule at pressures of 10 per square inch (psi) and 5 psi. The data on the gas according to the present disclosure shows a structural response at ~600 $cm^{-1}$ vs. percent transmittance % T indicating a change in structure. Regular water or divalent gasses, (such as $H_2$ or $O_2$,), do not show any structural response in the FTIR 600 cm-1 range, and the 600 $cm^{-1}$ response observed here in the gas according to the present disclosure increases proportionally with pressure, thus reconfirming that the IR response data at ~600 $cm^{-1}$ is proportional and real.

The peaks at 600.2 $cm^{-1}$ and 600.0 $cm^{-1}$ in the plots 902 show that the structurally altered gas molecule 160 has a unique structure different from the structure of the pure water vapor. In comparison, an FTIR molecular spectra of the pure water vapor has no peaks in the area around 600 $cm^{-1}$. Additionally, the peaks at 600 $cm^{-1}$ cannot be related to a diatomic gas because the FTIR of divalent gasses does not include peaks. Furthermore, the peaks at 600.2 $cm^{-1}$ and 600.0 $cm^{-1}$ are directly proportional to the observed gas molecule pressures recorded during the analysis. This proportionality substantiates that the peaks at 600.2 $cm^{-1}$ and 600.0 $cm^{-1}$ are caused by the pure structurally altered gas molecule 160 generated by the system 202 shown in FIG. 2.

Figure 10:
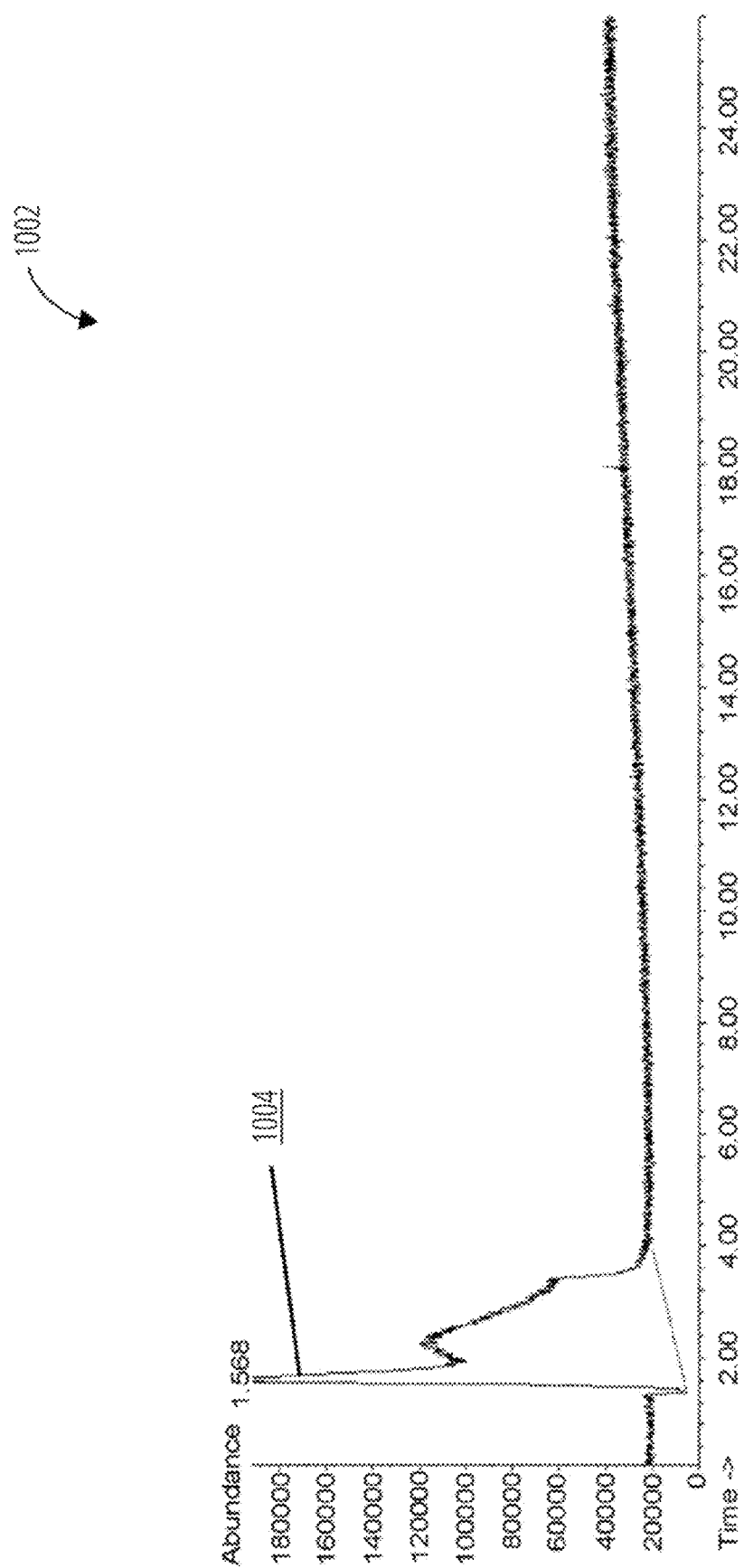
FIG. 10 illustrates a plot of gas chromatography—mass spectrometry measurements of peaks of regular water and gas infused water.
Figure 11:
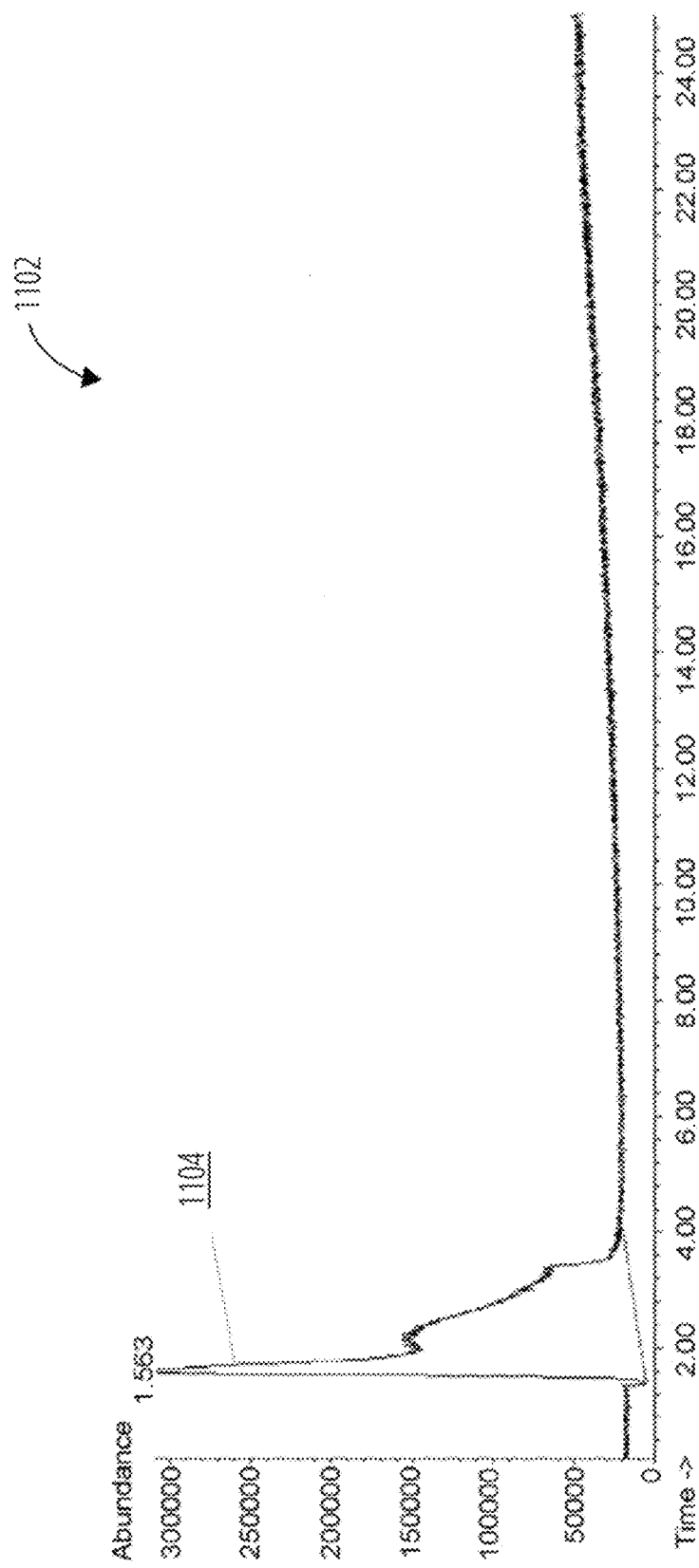
FIG. 11 illustrates a plot of gas chromatography—mass spectrometry measurements of peaks of regular water and gas infused water.

FIG. 10 shows a plot 1002 and FIG. 11 shows a plot 1102 of gas chromatography—mass spectrometry (GCMS) measurements of peaks of regular water 1004 and gas infused water 1104.

The first peak in the 1.56 range on the X axis (Time) shows an approximate 40% increase in value of Abundance, (Y axis) from 200,000 to 320,000 or ~37.5% in the chromatogram 610 (WA—water after infusion with the structurally altered gas molecule 160) as compared to the chromatogram 620 (WB—the water before the infusion). The second peak in the 2.20 range on the X axis (Time) shows an increase in Abundance, (Y Axis) from 120,000 for WB to 155,000 for WA or ~22.6%. These differences indicate structural change of the water treated by the structurally altered gas molecule. Specifically, the differences indicate differences in H—O bond length, H—O—H bond angle, and decreasing influence of hydrogen bond with the increase in vapor release in the GC-MS sample chamber.

Data in FIG. 10 and FIG. 11 indicates significant increase in the abundance (20K to 32K) at the ~1.56 time interval vs as well as the total abundance under the curve. This increase is directly proportional to the increase abundance of the gas in the water treated with the gas according to the present disclosure.

The measured and observed changes in the molecular structure of the gas in FIG. 10 and FIG. 11 enable it to possess non-polar behavior and accommodate more efficient electron sharing as MOT states.

The method according to the present disclosure provides an abundance of electrons for electron transport chain in living cells. It should also be noted in the experiment related to the application of a structurally altered gas molecule to enhance production of ATP in living organisms, where the only variable was introduction of the gas, resulted in a 25% increase in ATP production and a trend towards a decrease in hydrogen peroxide Reactive Oxygen Species (ROS) production during respiration supported by Complex II (0.00106 vs 0.00202 nmol $H_2O_2$/pmol $O_2$, p=0.089).

In another experiment conducted for the method according to the present disclosure, all other horses ran >15 min after drinking the water infused with structurally altered gas molecules. The same horses ran more than 2 mins longer (908±182 sec (T); 1047±232 sec (H)). $VO_2$ max was increased (94% probability) and their endurance was enhanced as reflected by the marked increase in the run time to fatigue in 7 of the 8 horses. These findings are compatible with and affirm the ex-vivo finding that mitochondrial ATP synthesis was enhanced in the presence of the water infused with structurally altered gas molecules. The reason for the improvement in stamina also may be that the saturation of the body with re-structured water infused with structurally altered gas molecules may have been associated with a reduction in the presence and/or effect of oxidants like ROS in the muscles. Reduced production of ROS in the long head of the triceps following consumption of the water infused with structurally altered gas molecules is compatible with an increase in the efficiency of ATP production due to the finished structure of the water infused with structurally altered gas molecules representing that of intracellular water.

In an example embodiment, the method according to the present disclosure may be used for degradation of PFAS contained in various states of matter with excess electrons and the resulting hydrated electrons. The method involves diffusing the gas generated by a generator of structurally altered gas molecules into a matter that can contain PFAS in solid, liquid, and gaseous media. The molecular alterations to generate and deploy the excess and resulting hydrated electrons generated by the generator. The electrons are accommodated by the lengthening of the H—O bonds from 0.95 Angstroms up to 1.3 Angstrom and decreasing the H—O—H bond angle from 104.5° to as small as 94°. These changes alter the chemical properties of the media that the gas may be infused into, furthering the ability of the hydrated electrons to target the PFAS. These changes include but are not limited to a decrease in normal pure water pH (from 7.0 to ~6.5), and a shift in redox potential from 0 mV to ~−200 mV. The negative ORP at a pH below 7 in the pure water confirms that excess electrons exist on their own without the negative ORP effect of dissolved anions in this gassed water. Hydrated electrons form when an excess of electrons is injected into liquid water.

Figure 12:
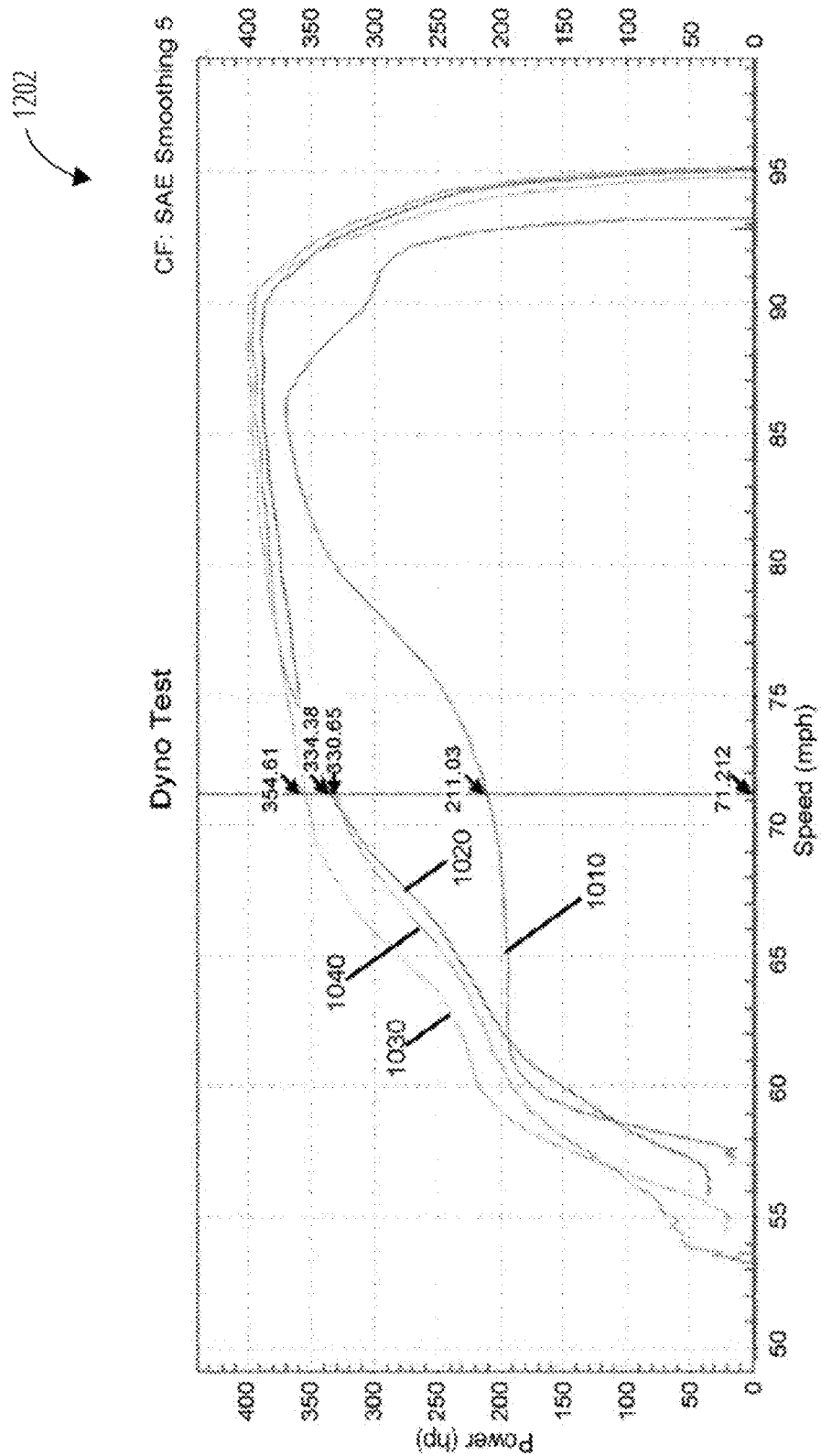
FIG. 12 is a diagram showing a dyno test analysis for an octane fuel with and without structurally altered gas molecule infusion.

FIG. 12 is a diagram 1202 showing a dyno test analysis for a 110 octane fuel with and without structurally altered gas molecule infusion. The line 1010 represents the untreated fuel (i.e., a fuel not infused with the structurally altered gas molecule) and the lines 1020, 1030, and 1040 are runs of the dyno test on the same 110 octane fuel infused with the structurally altered gas molecule. All dyno tests for the 110 octane fuel infused with the structurally altered gas molecule were performed at the same temperature, pressure, and conditions as those used for the dyno test of the untreated fuel. During the research, there was an average of 37.9% increase in horsepower (hp) at the 71.212 miles per hour mark on the dyno tests with the 110 octane fuel infused with the structurally altered gas molecule.

The empirical evaluation of the emissions associated with the untreated fuel and the 110 octane fuel infused with the structurally altered gas molecule (via a smell test) showed a significant decrease in unburned hydrocarbons and other undesirable emissions and smells shown by the 110 octane fuel infused with the structurally altered gas molecule.

In an example embodiment, the method according to the present disclosure may be applied to fossil and biofuels. The method produces a structurally altered gas molecule that exhibits non-polar properties, and therefore less dipole moment behavior (i.e., less existence of a negatively charged end and a positively charged end). When the structurally altered gas molecule is sufficiently mixed with other non-polar substances such as fossil fuels and biofuels, the structurally altered gas molecule disperse these fossil and biofuel molecules to make them available for a more complete combustion in a shorter time frame in the intended combustion area. The result is higher efficiency, more power and less $CO_2e$ formed by completing the combustion from methane and carbon monoxide to a lower $CO_2e$ valued product, carbon dioxide, and at the same time the inhibiting the formation of $NO_x$ and $SO_x$. Dyno testing on a fossil fuel engine, with the gas added (see line 1020, 1030, 1040 in FIG. 12) and without, (see line 1010 in FIG. 12) shows a horse power increase of efficiency of approximately 30%.

The abundance of electrons provided by the structurally altered gas molecule provide an environment where the lower activation energies of fossil fuels and biofuels, more specifically hydrogen (57 KJ/mole) and carbon (188 KJ/mole), can be achieved for complete combustion to carbon dioxide $CO_2$ and water $H_2O$. At the same time, there are sufficient available electrons provided by the method according to the present disclosure to inhibit the oxygen from taking the electrons from nitrogen and sulfur, inhibiting them from reaching their relatively higher activation energies to create $NO_2$ (400 KJ/mole) and $SO_2$ (297 KJ/mole). With the higher activation energies, nitrogen and sulfur are not oxidized, oxygen is not reduced, and the $NO_x$ and $SO_x$ compounds are not readily formed during combustion or as present in the exhaust.

FIG. 13 is a flow chart of a method 1300 for generation and deployment of a structurally altered gas molecules derived from water, according to an example embodiment. In some embodiments, the operations of the method 1300 may be combined, performed in parallel, or performed in a different order. The method 1300 may also include additional or fewer operations than those illustrated.

In block 1302, the method 1300 may commence with combining purified water with a compound mixture. The compound mixture may be non-reactive with the water and a conductor of an electric field and a magnetic field.

In block 1304, the method 1300 may proceed with applying the magnetic field and the electric field to the combination of the purified water and the compound mixture to cause generation of the structurally altered gas molecules. The structurally altered gas molecules have a higher probability of attraction of electrons into areas adjunct to the structurally altered gas molecules than molecules of the purified water. The structurally altered gas molecules are a combination of two parts of hydrogen and one part of oxygen. The structurally altered gas molecules have a hydrogen-oxygen-hydrogen bond angle between 94 degrees and 104 degrees and hydrogen-oxygen bond length between 0.95 Angstrom and 1.3 Angstrom. The structurally altered gas molecule is stable at a pressure exceeding 300 pounds per square inch gauge.

In block 1306, the method 1300 may include introducing the structurally altered gas molecules into an environment of a chemical process. The structurally altered gas molecules facilitate electron transfers during the chemical process, thereby increasing output of the chemical process.

In an example embodiment, the chemical process may include one or more of the following processes: generation of hydrogen, desalination of raw water, reduction of carbon oxide emissions during a fuel burn, degradation of polymers such as PFAS, production of adenosine tri phosphate in living organisms, and so forth.

In an example embodiment, the compound mixture may be in one of the following forms: in a liquid form, in a solid form, or in a gaseous form. In an example embodiment, the compound mixture is a combination of a solid, a liquid, and a gas.

Thus, systems and methods for generation and deployment of a structurally altered gas molecules derived from water have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A system for generation and deployment of structurally altered gaseous water molecules from water, the system comprising:

a first container for combining purified water with a compound mixture, the compound mixture being non-reactive with the water and a conductor for an electric field and a magnetic field, the compound mixture including a mixture of a hydroxide salt and an acid salt;

a magnetic field generator and an electric field generator designed to apply the magnetic field and the electric field to the combination of the purified water and the compound mixture to cause generation of the structurally altered gaseous water molecules, the structurally altered gaseous water molecules having a higher probability of attraction of electrons into areas adjunct to the structurally altered gaseous water molecules than molecules of the purified water; and a second container for introducing the structurally altered gaseous water molecules into an environment of a chemical process, wherein the structurally altered gaseous water molecules facilitate electron transfers during the chemical process, thereby increasing output of the chemical process.

2. The system of claim 1, wherein the chemical process includes generation of hydrogen.

3. The system of claim 1, wherein the chemical process includes desalination of raw water.

4. The system of claim 1, wherein the chemical process includes reduction of carbon oxide emissions during a fuel burn.

5. The system of claim 1, wherein the chemical process includes degradation of polymeric substances.

6. The system of claim 1, wherein the chemical process includes production of adenosine tri phosphate in living organisms.

7. The system of claim 1, wherein:

the structurally altered gaseous water molecules are a combination of two parts of hydrogen and one part of oxygen; and the structurally altered gaseous water molecules have a hydrogen-oxygen-hydrogen bond angle between 94 degrees and 104 degrees and hydrogen-oxygen bond length between 0.95 Angstrom and 1.3 Angstrom.

8. The system of claim 1, wherein the compound mixture is a combination of a solid, a liquid, and a gas.

9. The system of claim 1, wherein the structurally altered gaseous water molecules are stable at a pressure exceeding 300 pounds per square inch gauge.

10. The system of claim 1, wherein the compound mixture is in a liquid form.

11. The system of claim 1, wherein the compound mixture is in a gaseous form.

12. The system of claim 1, wherein the compound mixture is in a solid form.

\* \* \* \* \*